US005725523A

United States Patent [19]
Mueller

[11] Patent Number: 5,725,523
[45] Date of Patent: Mar. 10, 1998

[54] LATERAL-AND POSTERIOR-ASPECT METHOD AND APPARATUS FOR LASER-ASSISTED TRANSMYOCARDIAL REVASCULARIZATION AND OTHER SURGICAL APPLICATIONS

[76] Inventor: Richard L. Mueller, 1049 Kiel Ct., Sunnyvale, Calif. 94089

[21] Appl. No.: 627,704

[22] Filed: Mar. 29, 1996

[51] Int. Cl.[6] .................................................. A61B 17/36
[52] U.S. Cl. .................................. 606/15; 606/16; 607/89
[58] Field of Search ..................... 606/2, 3, 7; 607/13–17, 607/89; 128/642

[56] References Cited

U.S. PATENT DOCUMENTS

| | | | |
|---|---|---|---|
| 4,658,817 | 4/1987 | Hardy | 128/303.1 |
| 4,976,710 | 12/1990 | Mackin | 606/15 |
| 5,041,108 | 8/1991 | Fox et al. | 606/15 |
| 5,125,926 | 6/1992 | Rudko et al. | 606/19 |
| 5,217,454 | 6/1993 | Khoury | 606/14 |
| 5,249,574 | 10/1993 | Bush et al. | 607/9 |
| 5,380,316 | 1/1995 | Aita et al. | 606/7 |
| 5,389,096 | 2/1995 | Aita et al. | 606/15 |
| 5,425,355 | 6/1995 | Kulick | 606/14 |
| 5,549,601 | 8/1996 | McIntyre et al. | 606/15 |
| 5,573,531 | 11/1996 | Gregory | 606/14 |
| 5,607,421 | 3/1997 | Jeevanandam et al. | 606/7 |

OTHER PUBLICATIONS

Deckelbaum, "Cardiovascular Apps. of Laser Tech.",Lasers in Surgery and Medicine, 15:315–341 (1994).
Frazier et al., "Myocard. Revasc. with Las.", Cullen Cardio. Res. Labs., Tx. Heart Inst., Suppl. II C vol. 92, No. 9, II-58-65 (Nov. 1, 1995).

Primary Examiner—Jennifer Bahr
Assistant Examiner—Bryan K. Yarnell
Attorney, Agent, or Firm—Ray K. Shahani; Christopher N. Sears

[57] ABSTRACT

A balloon end contact scope device for performing laser-assisted transmyocardial revascularization (TMR) or other surgical and catheter procedures, the device particularly adapted for delivery of laser energy via a laser delivery means and configured to reach inside a body cavity or organ chamber at a point not directly accessible, either visually or otherwise, such as in a lateral or posterior position, the device having a hollow outer lumen, a balloon scope portion with an internal guide tube extending through the balloon portion for directing a laser delivery means or other surgical or catheter device through the visualization balloon toward the area being visualized. The balloon scope portion may have a plurality of guide holes extending therethrough. On the essentially transparent contact viewing surface a friction surface may be applied to facilitate precise positioning and treatment therethrough.

14 Claims, 6 Drawing Sheets

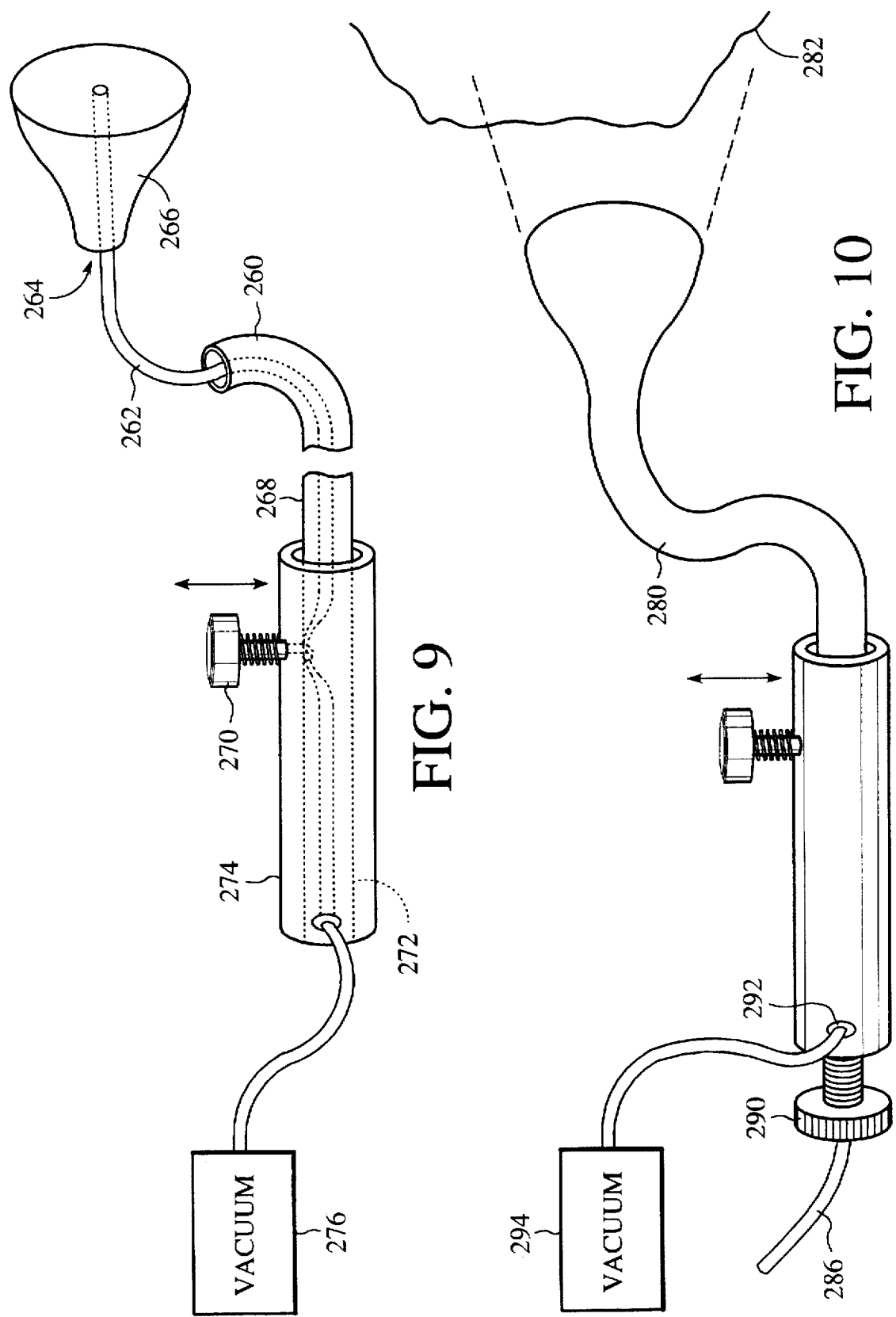

LATERAL-AND POSTERIOR-ASPECT METHOD AND APPARATUS FOR LASER-ASSISTED TRANSMYOCARDIAL REVASCULARIZATION AND OTHER SURGICAL APPLICATIONS

RELATED APPLICATIONS

This application is filed concurrently with U.S. patent application Ser. No. 08/627,701, still pending, and U.S. patent application Ser. No. 08/627,699, still pending, which applications are expressly incorporated herein in their entirety.

FIELD OF THE INVENTION

The present invention relates to the surgical procedure known as laser-assisted transmyocardial revascularization TMR), and more particularly, to improved methods and apparatuses for precisely positioning a fiber-optic or other waveguide adjacent the area or areas to be lased, including at positions adjacent the posterior epicardial and endocardial surfaces of the heart and at trans-septal positions within the chambers of the heart, thereby making possible the creation of channels in myocardial tissue at precisely the positions in the heart where ischemia or infarction or other have rendered such treatment desirable or necessary. These methods and apparatuses can be adapted for use in surgical applications throughout the human body or in animals for transmitting laser energy precisely, at predetermined positions and to predetermined depths.

BACKGROUND OF THE INVENTION

FIG. 1 is a schematic view of the human heart. The human heart 10 is a muscular dual pump that beats continuously throughout life sending blood to the lungs and the rest of the body. The interior of the heart consists of four distinct chambers. The septum 12, a thick central muscular wall, divides the cavity into right and left halves. On the fight side, the upper half is known as the right atrium 14. Deoxygenated blood from the rest of the body arrives in the right atrium via the vena cava 16, the blood is pumped across a one-way valve known as the tricuspid valve 18 into the lower portion known as the right ventricle 20. From there the blood circulates to the lungs through the pulmonary valve 22 via the pulmonary artery 24 where it is oxygenated by circulation through the alveoli of the lungs (not shown). The blood returns via the pulmonary veins to the left atrium 26 and flows through a second valve, the mitral valve 28 into the left ventricle 30 where it is pumped via the aorta 32 to the rest of the body.

Much of the heart consists of a special type of muscle called myocardium. The myocardium requires a constant supply of oxygen and nutrients to allow it to contract and pump blood throughout the vasculature. The inner surfaces of the chambers of the heart are lined with a smooth membrane, the endocardium, and the entire heart is enclosed in a tough, membranous bag known as the pericardial sac.

The pumping action of the heart has three main phases for each heart beat. Diastole is the resting phase during which the heart fills with blood: while deoxygenated blood is entering the right atrium oxygenated blood is returned from the lungs to the left atrium. During the atrial systole, the two atria contract simultaneously, squeezing the blood into the lower ventricles. Finally, during ventricular systole the ventricles contract to pump the deoxygenated blood into the pulmonary arteries and the oxygenated blood into the main aorta. When the heart is empty, diastole begins again. The electrical impulses which stimulate the heart to contract in this manner emanate from the heart's own pacemaker, the sinoatrial node. The heart rate is under the external control of the body's autonomic nervous system.

FIG. 2 is a schematic view of the coronary arteries on the outer surface of the human heart. Though the heart supplies blood to all other parts of the body, the heart itself has relatively little communication with the oxygenated blood supply. Thus, the two coronary arteries, the left coronary artery 40 and the right coronary artery 42 which arise from the aorta and encircle the heart muscle on either side "like a crown" to supply the heart itself with blood.

Heart disorders are a common cause of death in developed countries. They also impair the quality of life of millions of people restricting activity by causing pain, breathlessness, fatigue, fainting spells and anxiety. The major cause of heart disease in developed countries is impaired blood supply. The coronary arteries, which supply blood to the heart, become narrowed due to atherosclerosis and part of the heart muscle are deprive of oxygen an other nutrients. The resulting ischemia or blockage can lead to angina pectoris, a pain in the chest, arms or jaw due to a lack of oxygen to the heart, or infarction, death of an area of the myocardium caused by the ischemia.

Techniques to supplement the flow of oxygenated blood directly from the left ventricle into the myocardial tissue have included needle acupuncture to create transmural channels (see below) and implantation of T-shaped tubes into the myocardium. Efforts to graft the omentum, parietal pericardium, or mediastinal fat to the surface of the heart had limited success. Others attempted to restore arterial flow by implanting the left internal mammary artery into the myocardium.

Modernly, coronary artery blockage can be relieved in a number of ways. Drug therapy, including nitrates, beta-blockers, and peripheral vasodilator drugs (to dilate the arteries) or thrombolytic drugs (to dissolve the clot) can be very effective. If drug treatment fails transluminal angioplasty is often indicated - the narrowed pan of the artery, clogged with atherosclerotic plaque or other deposits, can be stretched apart by passing a balloon to the site and gently inflating it a certain degree. In the event drug therapy is ineffective or angioplasty is too risky (often introduction of a balloon in an occluded artery can cause portions of the atherosclerotic material to become dislodged which may cause a total blockage at a point downstream of the subject occlusion thereby requiring emergency procedures), the procedure known as coronary artery bypass grafting (CABG) may be indicated. CABG is the most common and successful major heart operation performed, in America alone over 500,000 procedures being performed annually. The procedure takes at least two surgeons and can last up to five hours. First, the surgeon makes an incision down the center of the patient's chest and the heart is exposed by opening the pericardium. A length of vein is removed from another pan of the body, typically the leg. The patient is connected to a heart-lung machine which takes over the function of the heart and lungs during the operation. The section of vein is first sewn to the aorta and then sewn onto a coronary artery at a place such that oxygenated blood can flow directly into the heart. The patient is then closed. Not only does the procedure require the installation of the heart-lung machine, a very risky procedure, but the sternum must be sawed through and the risk of infection is enhanced during the time the chest cavity is spread open.

Another method of improving myocardial blood supply is called transmyocardial revascularization (TMR), the creation of channels from the epicardial to the endocardial portions of the heart. The procedure using needles in a form of "myocardial acupuncture" has been experimented with at least as early as the 1930s and used clinically since the 1960s. Deckelbaum. L. I., Cardiovascular Applications of Laser technology. *Lasers in Surgery and Medicine* 15:315-341 (1994). The technique was said to relieve ischemia by allowing blood to pass from the ventricle through the channels either directly into other vessels perforated by the channels or into myocardial sinusoids which connect to the myocardial microcirculation. The procedure has been likened to transforming the human heart into one resembling that of a reptile.

In the reptile heart, perfusion occurs via communicating channels between the left ventricle and the coronary arteries. Frazier. O. H., Myocardial Revascularization with Laser - Preliminary Findings. *Circulation*, 1995; 92[suppl II]:II-58-II-65. There is evidence of these communicating channels in the developing human embryo. In the human hem, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous studies have been performed on TMR using lasers to bore holes in the myocardium. The exact mechanism by which blood flows into the myocardium is not well understood however. In one study, 20-30 channels per square centimeter were bored into the left ventricular myocardium of dogs prior to occlusion of the arteries. LAD ligation was conducted on both the revascularized animals as well as a set of control animals. Results showed that animals having undergone TMR prior to LAD ligation acutely showed no evidence of ischemia or infarction in contrast to the control animals. After sacrifice of the animals at ages between 4 weeks and 5 months, the laser-created channels could be demonstrated grossly and microscopically to be open and free of debris and scarring.

It is believed that the TMR channels occlude toward the epicardial surface but that their subendocardial section remains patent (unobstructed) and establishes camerosinusoidal connections. It is possible that the creation of laser channels in the myocardium may promote long-term changes that could augment myocardial blood flow such as by inducing angiogenesis in the region of the lased (and thus damaged) myocardium. Support of this possibility is reported in histological evidence of probable new vessel formation adjacent to collagen occluded transmyocardial channels. In the case of myocardial acupuncture or boring, which mechanically displaces or removes tissue, acute thrombosis followed by organization and fibrosis of clots is the principal mechanism of channel closure. By contrast, histological evidence of patent, endothelium-lined tracts within the laser-created channels supports the assumption that the inside of the laser channels is or can become hemocompatible and that it resists occlusion caused by thrombo-activation and/or fibrosis. A thin zone of charring occurs on the periphery of the laser-created transmyocardial channels through the well-known thermal effects of optical radiation on cardiovascular tissue. This type of interface may inhibit the immediate activation of the intrinsic clotting mechanisms because of the inherent hemocompatibility of carbon. In addition, the precise cutting action that results from the high absorption and low scattering of laser energy ($CO_2$, HO, etc.) may minimize structural damage to collateral tissue, thus limiting the tissue thromboplastin-mediated activation of the extrinsic coagulation.

U.S. Pat. No. 4,658,817 issued Apr. 21, 1987 to Hardy teaches a method and apparatus for TMR using a laser. A surgical $CO_2$ laser includes a handpiece for directing a laser beam to a desired location. Mounted on the forward end of the handpiece is a hollow needle to be used in surgical applications where the needle perforated a portion of tissue to provide the laser beam direct access to distal tissue.

U.S. Pat. No. 5,125,926 issued Jun. 30, 1992 to Rudko et al. teaches a heart-synchronized pulsed laser system for TMR. The device and method comprises a device for sensing the contraction and expansion of a beating heart. As the heart beat is monitored, the device triggers a pulse of laser energy to be delivered to the heart during a predetermined portion of the heartbeat cycle. This heart-synchronized pulsed laser system is important where the type of laser, the energy and pulse rate are potentially damaging to the beating heart or it's action. Often, application of laser energy to a beating heart can induce fibrillation or arrhythmia. Additionally, as the heart beats, it's spatial relationship between the heart and the tip of the laser delivery probe may change so that the necessary power of the beam and the required position of the handpiece may be unpredictable.

Finally, U.S. Pat. Nos. 5,380,316 issued Jan. 10, 1995 and 5,389,096 issued Feb. 14, 1995 both to Aita et al. teach systems and methods for intra-operative and percutaneous myocardial revascularization, respectively. The former patent is related to TMR performed by inserting a portion of an elongated flexible lasing apparatus into the chest cavity of a patient and lasing channels directly through the outer surface of the epicardium into the myocardium tissue. In the latter, TMR is performed by guiding an elongated flexible lasing apparatus into a patient's vasculature such that the firing end of the apparatus is adjacent the endocardium and lasing channels directly through the endocardium into the myocardium tissue without perforating the pericardium layer. These patents do not teach any method for controlling the elongated flexible laser delivery apparatus, nor do they teach methods of visualizing the areas of the heart being lased nor do they teach any method or devices for achieving TMR on surfaces or portions of the heart which are not directly accessible via a sternotomy, mini-sternotomy or via a trocar.

TMR is most often used to treat the lower left chamber of the heart. The lower chambers or ventricles are serviced by the more distal branches of the coronary arteries. Distal coronary arteries are more prone to blockage and resulting heart muscle damage. Roughly 50% of the left ventricle is direct line accessible through a thoracotomy or small incision between the ribs. However, roughly 50% is not direct line accessible and requires either rotating the heart or sliding around to the back side of the heart. Access to the heart is achieved by (1) sliding a device between the heart and pericardial sack which encases the heart, the device likely to have a 45-90 degree bend near the tip, (2) lifting the still beating heart, and (3) penetrating through the direct access side of the heart and/or through the septum of the heart. Lifting the still beating heart is less than desirable especially in patients with lowered heart performance. Furthermore, such manipulation can cause tachycardia (rapid beating of the heart absent undue exertion) fibrillation, arrhythmia or other interruptions in the normal beating cycle.

Thus, broadly, it is an object of the present invention to provide an improved method and device for laser-assisted TMR.

It is a further object of the present invention to provide an improved method and device for laser-assisted TMR in which the procedure may be carded out from within the interior of the heart and in which visualization or positioning of the laser delivery means is done by improved means.

It is a further object of the present invention to provide an improved method and device for laser-assisted TMR in which the procedure may be carried out on rear surfaces and other visually hidden external surfaces of the heart and in which visualization or positioning of the laser delivery means is done by improved means.

It is a further object of the present invention to provide an improved method and device for laser-assisted TMR in which the need for visualization during the procedure is minimized by employing a depth stop, such as a mesh basket or "moly bolt" device adjacent the end of the elongated flexible laser delivery means, to position the distal end of the laser delivery means It is a further object of the present invention to provide an improved method and device for laser-assisted TMR in which the distal end of the elongated flexible laser delivery means comprises a known visualization system with an adjunct visualization device to enhance the quality of the visualized image.

It is a further object of the present invention to provide an improved method and device for laser-assisted TMR in which the need for visualization during the procedure is minimized by deploying a mechanical or other tether coupled to the heart at a point adjacent to the area to be revascularized, thereby conveying the distal end of the laser delivery means to that area and maintaining it in a predetermined position during the creation of channels within the tissue of the myocardium.

SUMMARY OF THE INVENTION

A balloon end contact scope device for performing laser-assisted transmyocardial revascularization (TMR) or other surgical and catheter procedures, the device particularly adapted for delivery of laser energy via a laser delivery means and configured to reach inside a body cavity or organ chamber at a point not directly accessible, either visually or otherwise, such as in a lateral or posterior position, the device particularly adapted for use in conjunction with a visualization means, the device comprising a hollow outer lumen, the outer lumen having a proximal end and a distal end, the outer lumen suitable for conveying a surgical device such as for laser delivery or visualization. The device has a balloon scope portion, the balloon scope portion attached to the distal end of the device, the balloon scope portion comprising an essentially transparent contact viewing portion, a main body portion, the main body portion disposed between the contact viewing portion and the distal end of the outer lumen and attached to the distal end of the outer lumen, the attachments between the main body portion, the pre-contact viewing portion and the distal end of the outer lumen sealed to prevent introduction of fluids into the balloon scope portion, and a guide tube, the guide tube having a proximal end and a distal end, the distal end of the guide robe attached to the contact viewing portion and positioned such that it extends longitudinally toward the distal end of the outer lumen, the proximal end of the guide robe positioned to receive the distal end of a surgical or catheter device extending through the outer lumen, the guide suitable for conveying a surgical or catheter device through the balloon scope portion to the surface of the tissue being visualized through the contact viewing portion. In a preferred embodiment the outer lumen is rigid. In a preferred embodiment the outer lumen is flexible. In a preferred embodiment there is an inner lumen, the inner lumen having a proximal end and a distal end, the proximal end of the guide tube being attached to the distal end of the inner lumen such that a surgical or catheter device can extend through the inner lumen through the guide tube through the balloon scope portion to the surface of the tissue being visualized through the contact viewing portion. In a preferred embodiment there is a plurality of guide tubes, the guide tubes having proximal ends and distal ends, the distal ends of the guide tubes attached to the contact viewing portion and positioned such that they extend longitudinally toward the distal end of the outer lumen, the proximal ends of the guide tubes positioned to receive the distal end of a surgical or catheter devices extending through the device, the guides suitable for conveying the surgical or catheter devices through the balloon scope portion to the surface of the tissue being visualized through the contact viewing portion. In a preferred embodiment there is a plurality of inner lumens, the inner lumens having proximal ends and distal ends, the proximal ends of the guide tubes being attached to the distal ends of the inner lumens such that surgical or catheter devices can extend through the inner lumens of the device through the guide tubes through the balloon scope portion to the surface of the tissue being visualized through the contact viewing portion. In a preferred embodiment there is a laser delivery means, the laser delivery means extending through the outer lumen of the device and through the guide tube of the balloon scope portion for delivery of laser energy to the surface of the tissue being visualized through the contact viewing portion. In a preferred embodiment there is a plurality of laser delivery means, the laser delivery means extending through the outer lumen of the device and through the plurality of guide tubes of the balloon scope portion for delivery of laser energy to the surface of the tissue being visualized through the contact viewing portion. In a preferred embodiment there is a visualization means. In a preferred embodiment there is an inflating means, the inflating means suitable for introducing a suitable fluid such as air into the main body portion of the balloon scope portion. In a preferred embodiment the contact viewing portion of the balloon scope portion comprises a central high friction surface area and an peripheral low friction surface area, the central high friction surface area immediately adjacent to the attachment point between the distal end of the guide tube and the contact viewing portion, the low friction surface area disposed on the peripheral portions of the contact viewing portion such that when the balloon scope portion has a relatively low internal pressure the peripheral low friction surface area will come into contact with the tissue being visualized or treated and when the balloon scope portion has a relatively higher internal pressure the central high friction surface area of the contact viewing portion will come into contact with the tissue being visualized or treated. A preferred embodiment is adapted for use as a surgical instrument. A preferred embodiment is adapted for use as a catheter instrument.

A fluoroscope locator and guide tether device for use as a fluoroscopic marker or locator as wall as a guide tether for a monorail or other mounted-type fluoroscopic marking tools and materials, laser delivery means, visualization mean and other surgical equipment which can be positioned precisely along the guide tether adjacent tissue to be inspected or treated, thereby preserving spatial references In relation to the subject tissue, the device comprising a guide tether portion, the guide tether portion having a proximal end and a distal end and a predetermined length, the guide tether portion having a strength and thickness suitable for conveying fluoroscopic marking tools and materials, laser delivery means, visualization means and other surgical equipment along it's length, and a securing means, the securing means for securing the proximal end of the guide tether portion of the device to tissue or other structure adjacent the subject tissue being visualized, marked or otherwise treated. In a preferred embodiment the securing means is a suction cup. In a preferred embodiment the securing means is a tether clip. In a preferred embodiment the guide tether portion is made of a rigid material. In a preferred embodiment the guide tether portion is made of a flexible material. In a preferred embodiment there is a laser delivery means, the laser delivery means having a distal delivery end and capable of delivering laser energy in a predetermined beam position and pattern, the laser delivery means mounted on the guide tether portion of the device such that the guide tether portion acts as a monorail for conveying the distal delivery end of the laser delivery means to points adjacent the tissue or other structure being inspected or otherwise operated on. In a preferred embodiment the laser delivery means comprises a plurality of fiber optic cables. In a preferred embodiment there is a vacuum source, the vacuum source connected to the securing means, thereby maintaining the securing means attached to tissue or other structure by a vacuum seal. A preferred embodiment is adapted for use as a surgical instrument. A preferred embodiment is adapted for use as a catheter instrument.

A method of visualizing and treating the heart, other organs and internal parts of the human body comprising the following steps: (a) providing a balloon end contact scope with a main lumen and an essentially transparent contact viewing portion of a predetermined size and material of construction and integral laser delivery means or other equipment channel suitable for viewing the heart, other organs and internal parts of the human body; (b) precisely positioning the contact viewing portion in contact with a portion of the heart, other organ or internal body part adjacent the position to be viewed; and (c) visualizing the heart, other organ or internal body part. In a preferred embodiment the following step is included: (d) attaching a guide wire or tether to the heart, other organ or internal body part in order to locate a fluoroscopic or other visualization means or to perform additional visualization, fluoroscopic marking or other interventional procedure. In a preferred embodiment the portion of the heart, other organ or internal body part to be visualized or treated is on a lateral or posterior location on the heart, organ or other body part not directly visible or accessible via open surgery and other less-invasive techniques. In a preferred embodiment the following step is included: (e) delivering laser energy to the portion of the heart, other organ or internal body part to be treated via a laser delivery means introduced through the main lumen of the balloon end viewing scope. In a preferred embodiment the laser energy is delivered to the heart to effect transmyocardial revascularization. In a preferred embodiment step (b) is carried out by surgically placing the balloon end contact scope through an opening in the pericardial sac and adjacent the epicardial surface. In a preferred embodiment step (b) is carded out by placing the balloon end contact scope Into the vasculature of the patient and into an inner chamber of the heart.

A method of performing laser-assisted transmyocardial revascularization (TMR), the method utilizing a balloon end viewing scope with a central outer lumen to enhance visualization of surfaces being visualized or otherwise treated, the scope device having a means for delivering laser energy to the region being visualized, the method comprising the following steps: (a) surgically introducing a balloon end viewing scope into the chest cavity of a patient and through the pericardial sac of the heart to a position between the pericardial sac and the epicardial surface of the heart; b) precisely positioning the balloon end viewing scope adjacent an area of the epicardial surface from which revascularization is to be initiated, the precise positioning achieved through the use of a visualization means disposed within the balloon end viewing scope, visualization achieved through the transparent or partially transparent walls of the balloon structure pressed the epicardial surface; (c) positioning the distal end of a laser delivery means through the central lumen adjacent the area of the epicardial surface from which revascularization is to be initiated; and (d) delivering a controlled amount of laser energy directly onto the epicardial surface to create a TMR channel extending therethrough into the myocardium tissue. In a preferred embodiment the portions of the heart to be revascularized are located on the lateral and posterior sides of the heart.

A method of performing laser-assisted transmyocardial revascularization (TMR), the method utilizing a balloon end viewing scope with a central outer lumen to enhance visualization of surfaces being visualized or otherwise treated, the scope device having a means for delivering laser energy to the region being visualized, the method comprising the following steps: (a) introducing a balloon end viewing scope into the vasculature of a patient, for example at a point on the femoral artery, and into an internal chamber of the heart; (b) precisely positioning the balloon end viewing scope adjacent an area of the endocardium surface from which revascularization is to be initiated, the precise positioning achieved through the use era visualization means disposed within the balloon end viewing scope, visualization achieved through the transparent or partially transparent walls of the balloon structure pressed against the endocardium surface; (c) positioning the distal end of a laser delivery means through the central lumen adjacent the area of the endocardium surface from which revascularization is to be initiated; and (d) delivering a controlled amount of laser energy directly onto the endocardium surface to create a TMR channel extending therethrough into the myocardium tissue.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE DRAWINGS

FIG. 9 is a schematic view of a preferred embodiment of a suction cup-type fluoroscope locator and guide tether of the present invention.

FIG. 10 is a schematic view of the method of operation of a preferred embodiment of a suction cup-type fluoroscope locator and guide tether in conjunction with a dye swab advance mechanism, a laser delivery means advance mechanism, a balloon fill and evacuate built-in syringe mechanism and visualization aid of the present invention.

DETAILED DESCRIPTION OF THE PREFERRED EMBODIMENT

Figure 1:
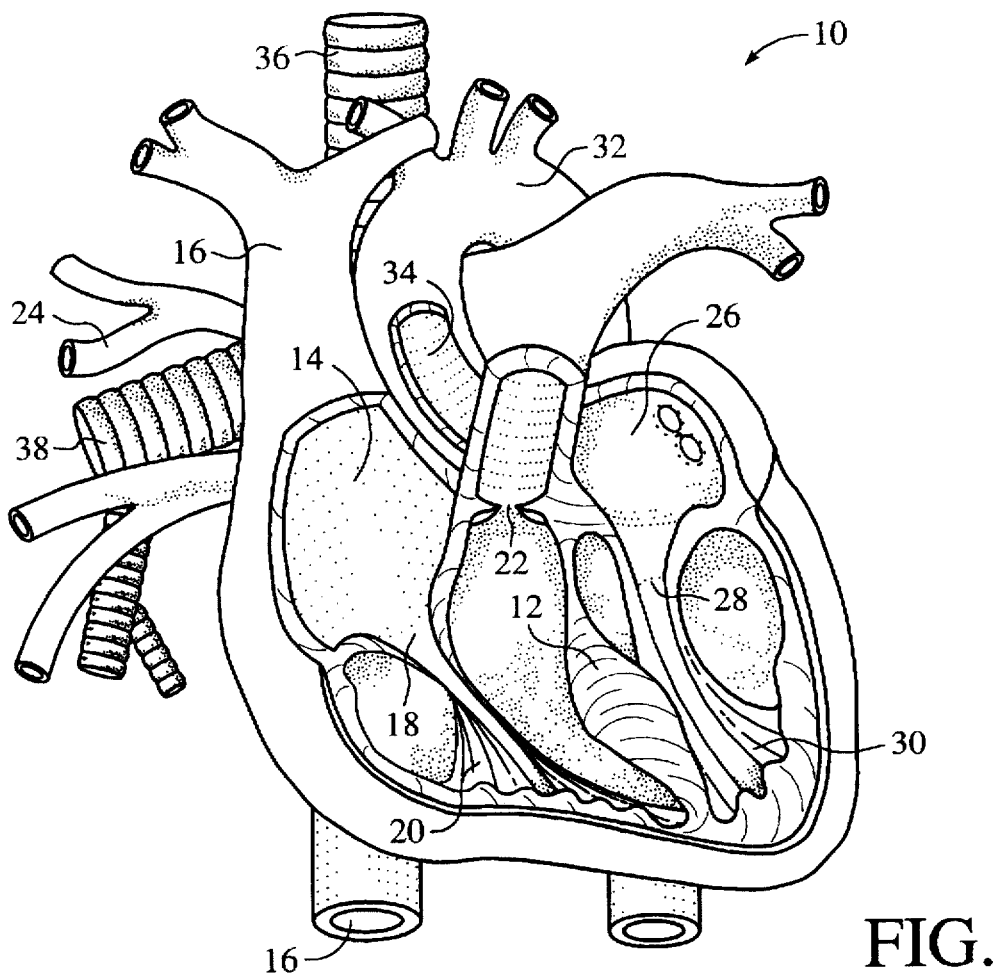
FIG. 1 is a schematic view of the human heart.
Figure 2:
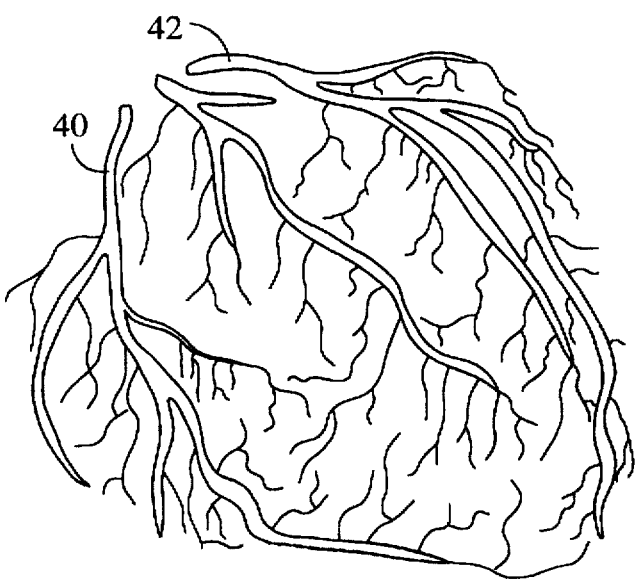
FIG. 2 is a schematic view of the coronary arteries on the outer surface of the human heart.
Figure 3:
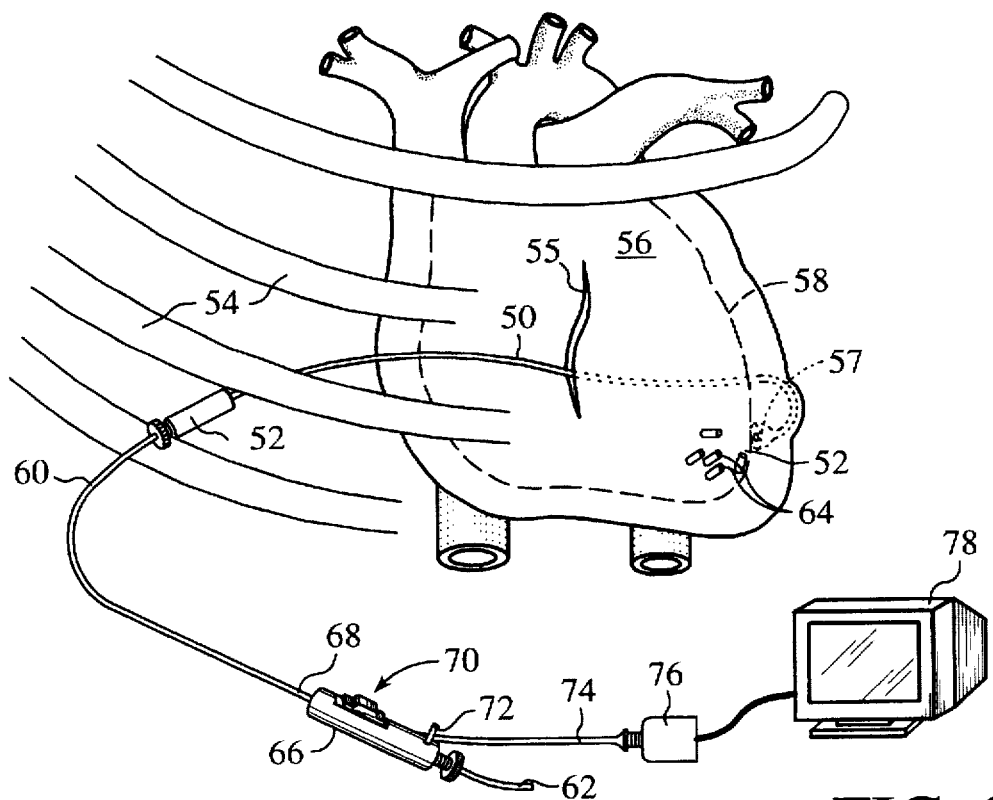
FIG. 3 is a cross section view of the human heart demonstrating a preferred method of TMR from the pericardium of the present invention.

FIG. 3 is a cross section view of the human heart demonstrating a preferred method of TMR in which access to the heart is gained by sliding the surgical device between the exterior surface of the heart and the pericardial sac containing the heart. As is well known in surgical methodology, the heart can be accessed externally via a mini-sternotomy perhaps with the use of a trocar or some other insertion tube device. The field of micro-surgery is advancing rapidly and small sophisticated tools can be introduced into the chest cavity through some type of catheter device. The device could contain a visualization probe, such as a 2-millimeter fiber bundle, a laser delivery means, and other accessories including a dye swab, guide tether, illumination, etc. In this drawing, the surgical device 50 is inserted through a trocar device 52 into the thoracic cavity between the ribs 54 of the patient. An incision 55 is made in the pericardial sac 56 and the surgical device is inserted therethrough. The balloon scope portion 57 is positioned adjacent the epicardial surface 58 of the heart. The surgical device would have a malleable stainless steel outer lumen 60. Inside the pericardial sac there is no blood in the space between the pericardial sac and the heart, however, the balloon still acts as a sliding surface and provides a suitable stand off distance for scope field of view. Thus, pushing blood out of the way is not a problem in this application, but holding the pericardium up like a tent is. The laser delivery means 62, optionally fiber optic or other waveguide, or other interventional or non-interventional surgical or catheter device would extend through with the balloon scope portion. As the laser energy is delivered to the adjacent epicardial surface, micro-channels 64 are produced in the surface of the epicardium, extending into the myocardium tissue and through the interior endocardium surface of the chamber in from of the laser beam.

The handle 66 of the surgical or catheter device is located at the proximal 68 end of the outer lumen. A laser delivery means advance lever 70 is located on and integral with the handle. Any means for controlling the fiber in a predetermined, precisely controllable manner will be useful and will be known to those skilled in the art. The laser delivery means advance means could also be located separately from the handle. A balloon inflation and deflation line 72 also attaches to the handle. The laser delivery means enters the surgical or catheter device. Visualization means includes a 2 millimeter fiber bundle 74 or other suitable scope, connected to a camera 76, which is introduced to the outer lumen of the surgical or catheter device. A video monitor 78 is useful for providing real-me images or other images as the procedure is taking place.

The surgical tip version can also be used for trans septal approach, i.e., the tip of the device is pushed through the surface of the heart and is used to treat the heart muscle from the inside out. In this case, the balloon is probably between about 2 to 3 centimeters in diameter, since turbulence becomes a problem for balloons significantly larger than that. In this case, since the ventricle is filled with blood, the balloon does provide visualization in those areas.

The balloon end contact scope and methods of the present invention will function equally well adapted to either surgical or catheter instruments, the distinction between the two being that catheter devices are generally considered to be devices used in the vasculature and other organ chambers of the body. A catheter tip would be smaller and adapted for introduction using percutaneous techniques. The catheter tip version would typically have a balloon end of less than about 1 centimeter diameter, and would be built on a braided or laminated urethane or other suitable material lumen for push and torque.

Figure 4:
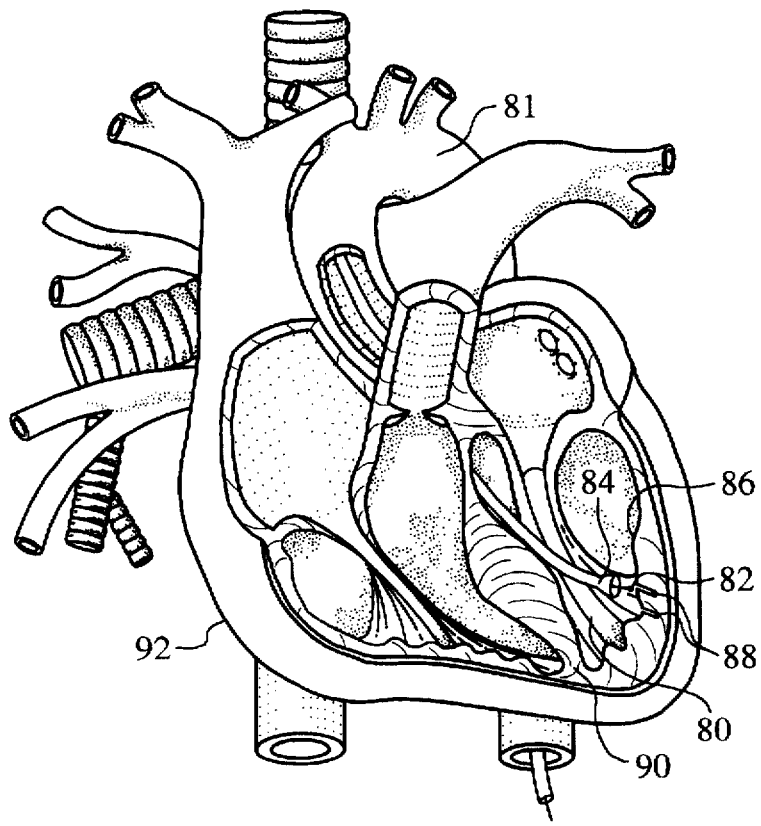
FIG. 4 is a cross section view of the human heart demonstrating a preferred method of TMR from the endocardium of the present invention.

FIG. 4 is a cross section view of the human heart demonstrating a preferred method of TMR from the endocardium of the present invention. In this procedure, the left ventricle 80 is internally accessed via the aorta, the catheter device optionally introduced via the femoral artery or otherwise. The laser delivery 82 device extending from the outer lumen 84 of the catheter device is positioned adjacent the endocardium surface 86. Micro-channels 88 are lased into the myocardium tissue 90 but do not perforate the epicardial surface 92. Visualization through the balloon end contact scope portion 94 of the catheter device is improved over conventional catheter devices or scopes. In this manner, the chamber filled with blood or other organ cavities can be accessed, probed and treated with more precision and control than heretofore possible.

Figure 5A:
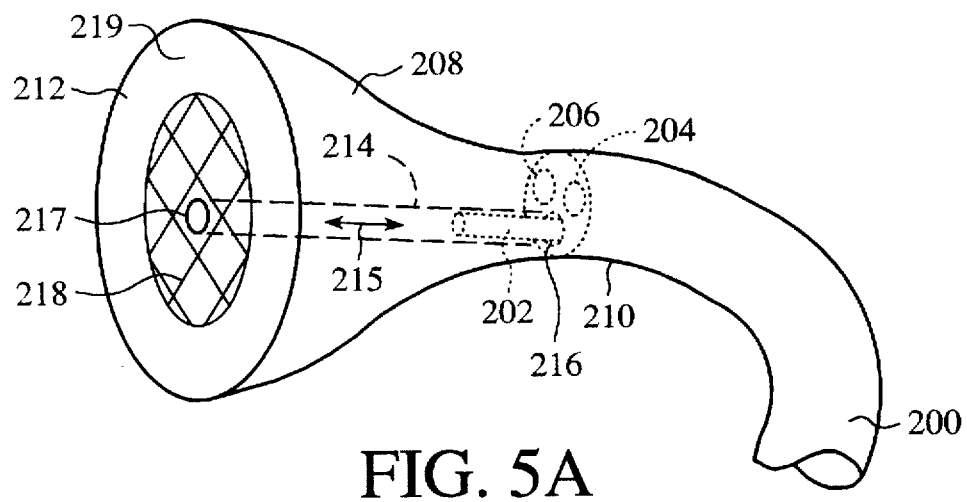
FIG. 5A is a schematic view of a preferred embodiment era balloon end contact scope of the present invention.

FIG. 5A is a schematic view of a preferred embodiment of a balloon end contact scope of the present invention. In this novel device, visualization of the surface being contacted is greatly enhanced. A stainless steel or other material malleable shaft 200 comprises the outer lumen of the catheter device. This semi-rigid lumen can be introduced into the chest cavity through a mini-sternotomy or trocar device and then positioned adjacent the posterior surface of the heart. In this manner, TMR can be performed on a portion of the heart otherwise visually inaccessible. For exemplary purposes, the surgical or catheter device is shown including an interventional device 202, such as a laser delivery means, and a viewing scope port 204, such as for a 2 millimeter fiber bundle. Either the entire surgical or catheter device could be pressurized or the device could also have a balloon fill port 206. The balloon 208 is attached to the distal end 210 of the device. Between the distal end of the device and the contact surface portion 212 of the balloon there is an extruded laser delivery means guide tube 214 with a central axis 215, proximal end 216 and distal end 217. Once the balloon is placed against the heart surface, blood is squeezed away and a clear, unobstructed view of the area being lased can be obtained with the viewing scope or fiber bundle. Providing a high friction surface 218 in the central portion of the contact surface portion will assist the surgeon maintain the balloon in place during delivery of laser energy, visualization, etc. A low friction surface 219 can be placed around the perimeter of the contacting surface portion. A similar smaller scale tip can be affixed to a catheter shaft or lumen and be introduced via percutaneous catheter techniques, as shown in FIG. 4.

This device can be configured as either a catheter device or as a surgical took A catheter balloon end will be smaller (between about ½ and 1 centimeter) than that of a surgical tool (between about 1 and 3 centimeters). A surgical tool would have a malleable stainless steel tubing construction, or similar. A catheter device might have a braided-laminate or other high push, high torque sustaining material or structure construction.

Figure 5B:
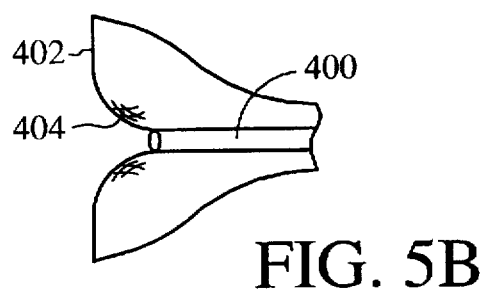
FIG. 5B is a detail view era balloon end contact scope of the present invention.

FIG. 5B is a detail view of a balloon end contact scope of the present invention. In this embodiment, the guide tube 400 is designed to be somewhat shorter in relation to the shape of the balloon. In the prior figure, the profile of the inflated balloon was fairly perpendicular to the central axis of the guide tube. In this embodiment, when a lower internal pressure is used, the balloon end scope contacts the surface of the area being visualized at the outer perimeter low friction surface 402 and the high friction surface area 404 is kept from contacting the tissue surface. In this modality the end of the scope can slide easily over surface areas being visualized.

Figure 5C:
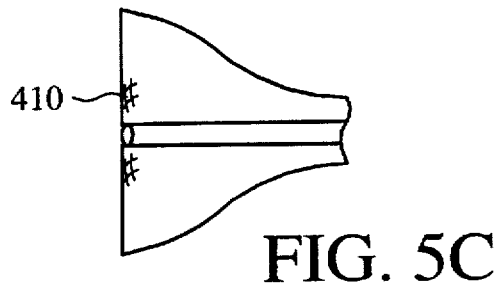
FIG. 5C is a detail view of a balloon end contact scope of the present invention.

FIG. 5C is a detail view of a balloon end contact scope of the present invention. In this embodiment, a higher internal balloon pressure is utilized to fully expand the balloon. In this modality, the high friction surface area 410 will come in contact with the adjacent tissue and will assist the surgeon maintain the balloon in place during delivery of laser energy, visualization, etc.

Figure 6:
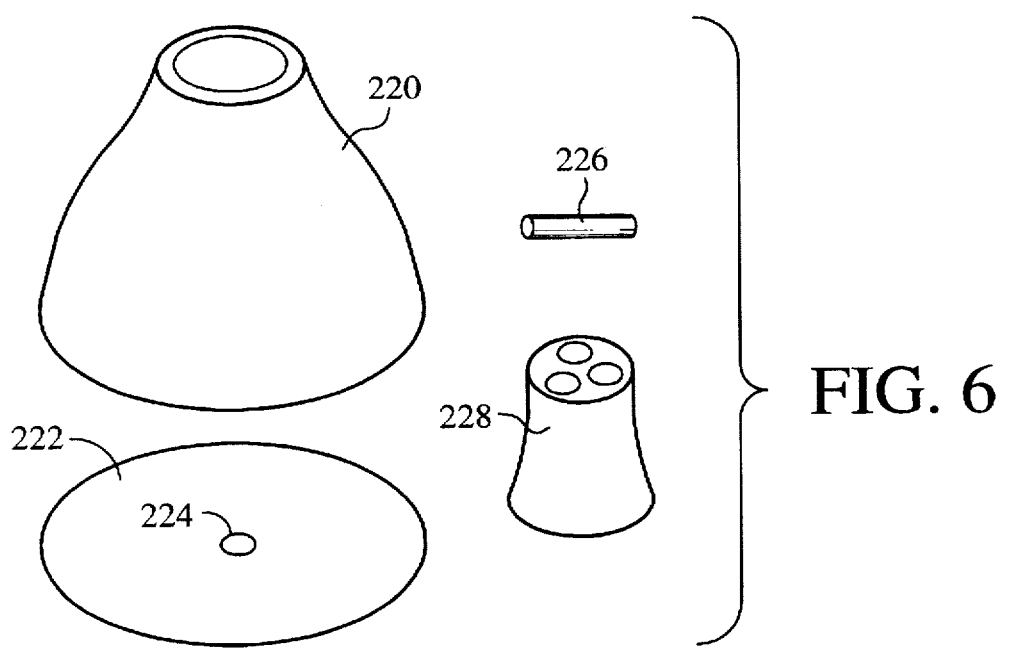
FIG. 6 is a graphic representation of the various components of assembly of a preferred embodiment of a balloon end contact scope of the present invention.

FIG. 6 is a graphic representation of the various components of assembly of a preferred embodiment of a balloon end contact scope of the present invention. The main body portion 220 of the balloon scope portion of the catheter device can be made of a flexible film of any suitable material, including urethane, nylon, rubber, plastic, etc. The contact surface portion 222 could be made of the same material or of a different material which allows for fiber scope visualization through the balloon contact wall. The contact surface portion can be sealed to the laser delivery means guide tube 224 such that the guide tube terminates at an opening 226 in the contact surface. The main body portion of the balloon scope portion is sealed to the outer perimeter of the contact viewing portion and the distal end of the adapter fitting 228 by any of various known or unknown, suitable sealing means, including RF, thermal, polymeric or other.

It will be obvious to those skilled in the art that the above-described combination of elements comprising the balloon scope portion of the catheter device of the present invention can be modified and adapted to any of various similar designs. The main body portion, contact viewing portion and adapter fitting can be integrated into a single "balloon"-type structure, or additional construction elements can be added to provide a balloon scope portion of a predetermined size, shape, orientation, flexibility, rigidity or transparency. Furthermore, the balloon scope portion of the catheter device can have mechanical, electrical, thermal, optical or acoustic sensors, transducers, transceivers or other type of coupling device for determining ambient temperature, electrical activity, heart rate and pulse cycle, organ function and/or other parameters necessary or useful for performing TMR or other surgical procedures within the human or other animal body.

Figure 7:
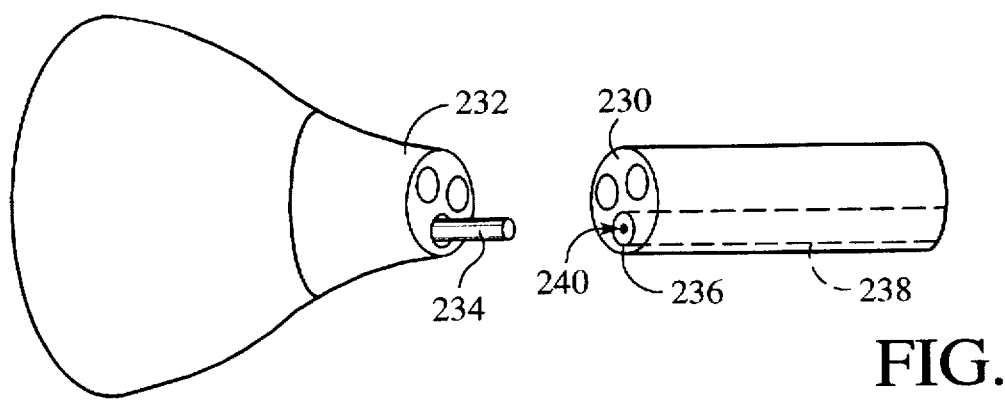
FIG. 7 is a schematic view of a preferred embodiment of the interface between a balloon end contact scope of the present invention and a lumen tip housing the distal end of a laser delivery means and a visualization scope.

FIG. 7 is a schematic view of a preferred embodiment of the interface between a balloon end contact scope of the present invention and a lumen tip housing the distal end of a laser delivery means and a visualization scope. This view clearly shows the connection which must be made between the distal end 230 of the catheter device and the adapter fitting 232 of the balloon end contact scope of the present invention. The proximal end 234 of the laser delivery guide tube must be sealed to the distal end 236 of the laser delivery means inner lumen 238. The laser fiber delivery device 240, or other interventional device, will extend through the proximal end of the laser delivery means guide tube and as the balloon scope is pressed against the heart surface to be lased, the position of the laser delivery means can be visualized and controlled precisely.

Figure 8:
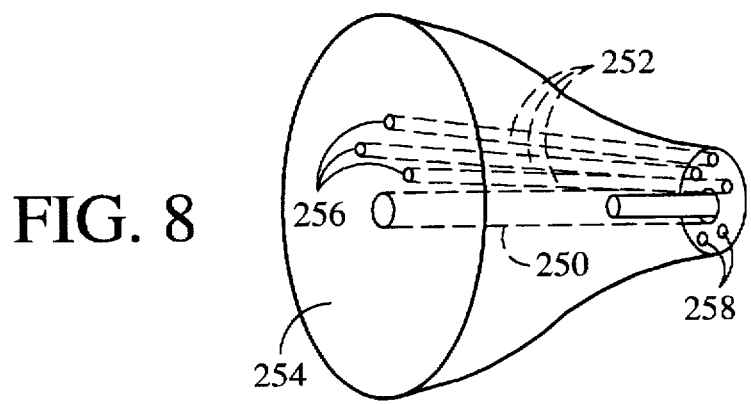
FIG. 8 is a schematic view of a preferred embodiment of a balloon end contact scope having a patterning device built into the tip of the balloon of the present invention.

FIG. 8 is a schematic view of a preferred embodiment of a balloon end contact scope having patterning guides built into the tip of the balloon of the present invention. In this embodiment, in addition to a laser delivery means or other interventional device central guide tube 250, there are an additional plurality of laser delivery guide tubes 252 extending through the balloon and attached to the balloon contacting surface 254 at certain, predetermined positions 256. The precise positions can be selected as desired, the group of three fibers or other waveguides shown in the figure being representative of a preferred embodiment. Furthermore, it will be understood that in addition to or instead of laser delivery means, other micro-surgical instruments may be useful or required for certain procedures, including irrigation, visualization, dye swabbing, marking or scanning, or other general or specific access to an internal organ. The balloon access ports 258 will also be used.

FIG. 9 is a schematic view of a preferred embodiment of a suction cup-type fluoroscope locator and guide tether of the present invention. This device serves multiple uses, including use as a fluoroscopic marker or locator as well as a guide tether for a monorail-type mounted catheter device which can be positioned precisely thereby. This is important because spatial references are easily lost when working through long ports, using cameras and tools with bends. Marking might help the surgeon developing a certain expertise performing TMR or other procedures. Extending through a malleable lumen 260 which forms the outer lumen of the device, a thin floppy vacuum line and tether 262 is attached at its distal end 264 to a soft rubber suction cup 266. It will be understood that the materials of construction for the various components may be rigid, semi-rigid or flexible materials, as might be indicated. In the preferred embodiment the suction cup or a portion thereof might be filled with a radio-opaque material, such as 20% barium or bismuth solution, or other materials. In this manner, the position of the suction cup can be determined precisely using known methods of fluoroscopy. At the proximal end 268 of the malleable lumen, or some other position, a spring-loaded pin 270 extends into a channel 272 in the mechanism housing 274, thereby pinching the tube in certain configurations. A source of vacuum 276 would be used.

FIG. 10 is a schematic view of a preferred embodiment of the device and method of performing TMR or other procedure. The system includes a suction cup-type fluoroscope locator and guide-tubing tether 280 anchored to tissue 282 adjacent the area being viewed or lased. A dye swab 286 could be advanced through access port 290. The access port is rotatably opened or closed constricting o-ring 292 to provide a vacuum tight but slidable seal on the advancing dye swab. A vacuum source 294 would also be used. This embodiment converts fluoroscopic location of the suction cup to a visual heart surface identifier for subsequent use of product as shown in FIG. 5A.

Figure 11:
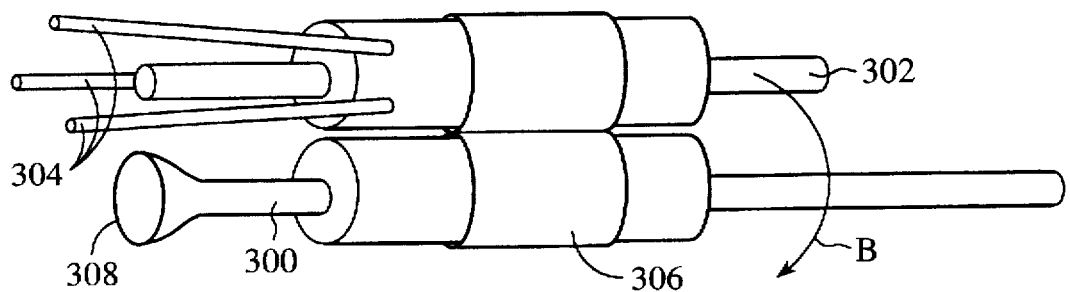
FIG. 11 is a schematic view of a preferred embodiment of a suction cup-type fluoroscope locator and guide tether in conjunction with a catheter device of the present invention having a plurality of laser delivery means extending therefrom of the present invention.

FIG. 11 is a schematic view of a preferred embodiment of a suction cup-type fluoroscope locator and guide tether 300 in conjunction with a surgical device 302 of the present invention. The device has a plurality of laser delivery means 304 extending therefrom. The device has a slider 306 which rides on the tether up to the point where the suction cup 308 or attachment clip is attached to the tissue adjacent the area to be lased. Rotation of the device in a direction B about the point of attachment by the suction cup portion onto the tissue will be facilitated.

Figure 12:
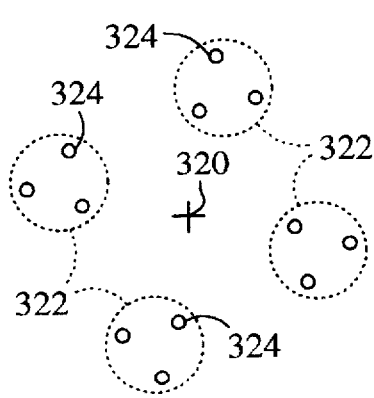
FIG. 12 is a graphical representation of the beam pattern and channels created by a catheter device with a plurality of laser delivery means extending therefrom.

FIG. 12 is a graphical representation of the beam pattern and channels created by a catheter device with a plurality of laser delivery means extending therefrom. As will be apparent to those skilled in the art, it is possible to anchor the device to the subject tissue at a tether anchor point x, for example, and then lase the tissue with all of the extending laser delivery means simultaneously. Once a first set (denoted by the dashed lines 322) of channels 324 are created, slight re-orientation of the device about the attachment point will position the extending laser delivery means to create a new set of channels in a position precisely defined in spatial relation to the tether anchor point. A series of channel sets can be created completely around the tether anchor point and revascularization at any indicated channel density in a given, precisely determined position can be achieved.

Figure 13:
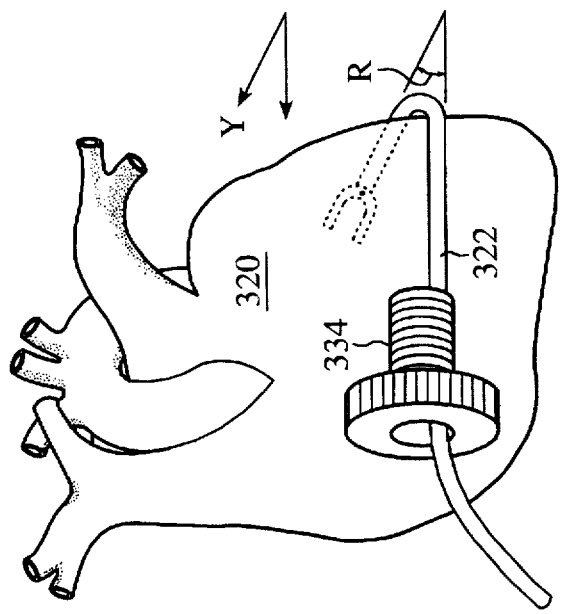
FIG. 13 is a schematic view of a preferred embodiment of a lateral aspect positioning device of the present invention for use with fluoroscope locaters and guide tethers.

FIG. 13 is a schematic view of a preferred embodiment of a lateral aspect positioning device applicator of the present invention for use with fluoroscope locators and guide tethers. In this view, it is shown how parts of the heart 320 or any other organ or body part being worked on or near or behind are often situated in such a way as to make direct visualization impossible. In moden, less-invasive surgical techniques it is impossible to manipulate the organ in the same way as if performing the procedure via an open chest cavity. In this view, a clip or other tether locator device applier 322 inserted, optionally through a trocar device 324. The applier has a bend at one end, with a given radius R and angle of orientation Y. Though there might be a plurality or bends or curves in the tether applier device, as appropriate for the procedure being performed, a standard radius of curvature might be between about 1 and 5 inches and the angle of orientation between about 45 and 120 degrees. The device can reach around to the back of the heart or other organ or orifice to attach a tether clip or suction cup or perform a marking or other function.

Figure 14:
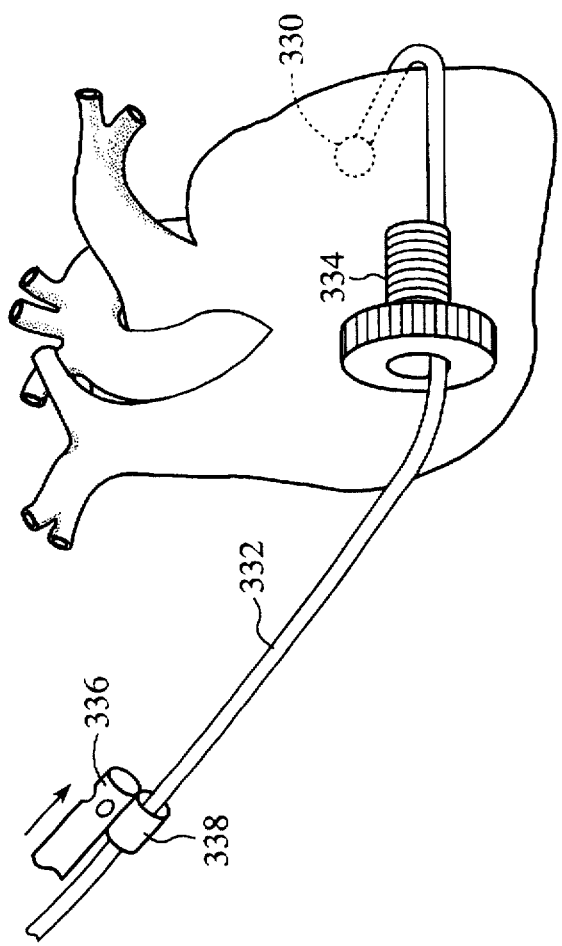
FIG. 14 is a schematic view of the method of operation of a preferred embodiment of a fluoroscope locator and guide tether in conjunction with a monorail-type mount surgical or catheter device of the present invention.

FIG. 14 is a schematic view of the method of operation of a preferred embodiment of a fluoroscope locator and guide tether in conjunction with a monorail-type mount catheter device of the present invention. Once in place, in this view attached to a tether anchor point 330 in the back of the heart, the guide tether 332 leads back through the trocar device 334, if used. Along the tether a catheter device 336 with a slider 338 can be slid along the tether through the trocar device or other entry point to the chest cavity or vasculature, and positioned adjacent the guide tether anchor point.

Figure 15:
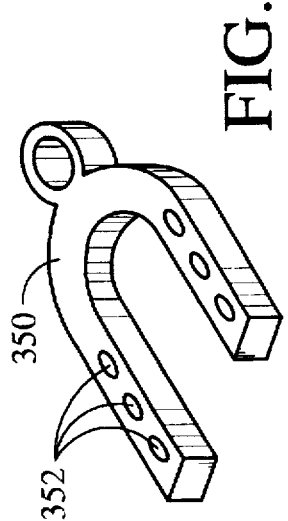
FIG. 15 is a schematic view of a preferred embodiment of a guide tether clip of the present invention having surface coining.

FIG. 15 is a schematic view of a preferred embodiment of a guide tether clip of the present invention having surface coining. In addition to the suction cup-type fluoroscopic marker and tether anchor, the guide can also be anchored to the heart other tissue, bone or other structure with a removable clip 350. Made out of metal, plastic, special radio-opaque or other suitable material. Coining marks 352 are often useful to enhance the gripping quality of the clip. These marks could be made in the molding or forming process, or stamped in or otherwise applied after fabrication.

Figure 16:
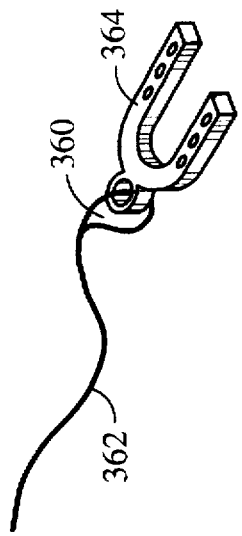
FIG. 16 is a schematic view of a preferred embodiment of a guide tether and clip of the present invention.

FIG. 16 is a schematic view of a preferred embodiment of a guide tether and clip of the present invention. In this view, the distal end 360 of the tether 362 is shown attached to the removable clip 364. It will be understood by those skilled in the art that the materials of construction, dimensions and methods of using these systems may be modified to suit the particular patient's needs, the surgeon's expertise and preferred procedure, etc.

The present invention is intended for use with any medical laser. In particular, the Holmium laser, including many of various different types known and available now or at any time, will be particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this application.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A contact scope device for performing a transmyocardial revasculariztion (TMR) procedure comprising:

a hollow outer lumen having a proximal end and a distal end;

a scope portion located at the distal end of the contact scope device, the scope portion including:

a contact viewing portion for contact with a wall of the heart, the contact viewing portion defining at least one port adapted for receiving at least one TMR working component for performing TMR on the wall of the heart, the contact viewing portion further including a friction surface area for gripping tissue adjacent the heart wall and providing stability for the contact viewing scope during the TMR procedure;

a main body portion disposed between the contact viewing portion and the distal end of the outer lumen; and visualization means for viewing tissue of the wall of the heart through the contact viewing portion.

2. The device of claim 1 wherein at least a portion of the outer lumen is rigid.

3. The device of claim 1 wherein at least a portion of the outer lumen is flexible.

4. The device of claim 1 further comprising at least one guide tube extending at least through the scope portion and providing a pathway for the at least one TMR working component.

5. The device of claim 4 having a plurality of guide tubes and ports, the guide tubes having proximal ends and distal ends the distal ends of the guide tubes communicating with the ports in the contact viewing portion, the proximal ends of the guide tubes positioned to receive the distal ends of multiple TMR working components, whereby the plurality of guide tubes convey the multiple TMR working components through the scope portion to the tissue being visualized.

6. The device of claim 5 further comprising a plurality of inner lumens, the inner lumens having proximal ends and distal ends, the proximal ends of the guide tubes being attached to the distal ends of the inner lumens such that the multiple TMR working components can extend through the inner lumens, through the guide tubes in the scope portion to a surface of the tissue being visualized.

7. The device of claim 5 wherein the multiple TMR working components are a plurality of laser delivery devices.

8. The device of claim 1 wherein the at least one TMR working component is at least one laser delivery device extending through the outer lumen of the scope device and through the scope portion for delivery of laser energy to tissue.

9. The device of claim 1 wherein the visualization means is a viewing fiber optic bundle within the scope portion.

10. The device of claim 1 wherein the scope portion is inflatable by an inflating means for introducing a fluid into the scope portion.

11. The device of claim 1 wherein the friction surface area has a relatively high friction surface area and a low friction surface area, the friction surface area is on peripheral portions of the contact viewing portion, whereby when the scope portion has a relatively low internal pressure, the low friction surface area contacts observed tissue and when the scope portion has a relatively higher internal pressure, the high friction surface area of the contact viewing portion contacts the tissue.

12. The device of claim 1 wherein the device is a surgical instrument insertable through a trocar.

13. The device of claim 1 wherein the device is a catheter instrument.

14. A contact scope device with a tissue ablation device for performing a transmyocardial revasculariztion (TMR) procedure comprising:

a hollow outer lumen having a proximal end and a distal end;

a scope portion located at the distal end of the contact scope device, the scope portion including:

a contact viewing portion for contact with a wall of the heart, the contact viewing portion defining at least one port adapted for receiving at least one optical fiber for performing tissue ablation using laser irradiation on the wall of the heart, the contact viewing portion further including a friction surface area for gripping tissue adjacent the heart wall and providing stability for the contact viewing scope during the TMR procedure;

a main body portion disposed between the contact viewing portion and the distal end of the outer lumen; and visualization means for viewing tissue of the wall of the heart through the contact viewing portion.

* * * * *